US007341567B2

(12) United States Patent
D'Amico

(10) Patent No.: US 7,341,567 B2
(45) Date of Patent: Mar. 11, 2008

(54) TRACTION DEVICE FOR PHYSICAL THERAPY

(76) Inventor: Anthony T. D'Amico, 362 Eckford, Troy, MI (US) 48084

(*) Notice: Subject to any disclaimer, the term of this patent is extended or adjusted under 35 U.S.C. 154(b) by 518 days.

(21) Appl. No.: 10/659,552

(22) Filed: Sep. 10, 2003

(65) Prior Publication Data

US 2004/0092854 A1 May 13, 2004

Related U.S. Application Data

(60) Provisional application No. 60/409,519, filed on Sep. 10, 2002.

(51) Int. Cl.
*A61F 5/04* (2006.01)
*A61F 5/045* (2006.01)

(52) U.S. Cl. .......................................... 602/33; 606/241

(58) Field of Classification Search ............ 602/32–38; 606/237, 240, 241
See application file for complete search history.

(56) References Cited

U.S. PATENT DOCUMENTS

| | | | | | |
|---|---|---|---|---|---|
| 1,205,649 | A | * | 11/1916 | Miller | 606/241 |
| 1,765,669 | A | * | 6/1930 | Henze et al. | 602/32 |
| 2,186,036 | A | * | 1/1940 | Peachey | 602/33 |
| 2,230,620 | A | * | 2/1941 | Leiter | 602/33 |
| 2,633,125 | A | * | 3/1953 | Yellin | 602/36 |
| 2,712,820 | A | * | 7/1955 | Robinson | 602/36 |
| 2,773,499 | A | * | 12/1956 | Zur Nieden | 602/32 |
| 2,837,085 | A | * | 6/1958 | Tong | 602/32 |
| 2,910,061 | A | * | 10/1959 | Rabjohn | 602/33 |
| 2,954,026 | A | | 9/1960 | Spinks | |
| 3,003,498 | A | | 10/1961 | Hotas | |
| 3,033,198 | A | * | 5/1962 | Jensen | 602/33 |
| 3,086,518 | A | * | 4/1963 | Barlow et al. | 602/32 |
| 3,105,489 | A | | 10/1963 | Zivi | |
| 3,114,366 | A | | 12/1963 | Maychark | |
| 3,149,630 | A | | 9/1964 | Schmidt | |
| 3,167,068 | A | * | 1/1965 | Carr | 602/32 |
| 3,403,675 | A | * | 10/1968 | Carr | 602/32 |
| 3,413,971 | A | * | 12/1968 | Evans | 602/32 |
| 3,616,795 | A | * | 11/1971 | Powlan | 602/35 |
| 3,667,457 | A | | 6/1972 | Zumaglini | |
| 3,680,551 | A | * | 8/1972 | Bell et al. | 602/36 |
| 3,765,411 | A | * | 10/1973 | Ward, Jr. | 602/35 |
| 3,871,366 | A | | 3/1975 | Cotrel | |
| 3,888,243 | A | * | 6/1975 | Powlan | 602/33 |
| 3,905,359 | A | | 9/1975 | Fanstone | |
| 3,937,216 | A | * | 2/1976 | Brown | 602/32 |
| 4,114,611 | A | * | 9/1978 | Lyle et al. | 606/241 |
| 4,166,459 | A | | 9/1979 | Nightingale | |
| 4,266,537 | A | * | 5/1981 | Bonin et al. | 602/32 |
| 4,538,598 | A | * | 9/1985 | Gill et al. | 602/33 |
| 4,539,979 | A | * | 9/1985 | Bremer | 602/32 |
| 4,593,684 | A | | 6/1986 | Graham | |
| 4,606,333 | A | | 8/1986 | Graham | |
| 4,627,423 | A | * | 12/1986 | Kampner | 602/35 |
| 4,664,099 | A | * | 5/1987 | Pearl, Jr. | 602/35 |

(Continued)

*Primary Examiner*—Danton DeMille
(74) *Attorney, Agent, or Firm*—Young Basile P.C.

(57) ABSTRACT

A traction device for use on a support surface which includes a body contacting assembly which releasably contacts the a suitable anatomical region of the patient, a gas spring and associated assembly, the gas spring variable between an extended rest position and a contracted force exerting position, and means of relieving traction force exerted by the gas spring and associated assembly.

25 Claims, 5 Drawing Sheets

U.S. PATENT DOCUMENTS

| | | | | | |
|---|---|---|---|---|---|
| 4,674,485 | A | * | 6/1987 | Swanson | 602/33 |
| RE32,791 | E | * | 11/1988 | Saunders | 602/32 |
| 4,784,122 | A | | 11/1988 | Graham | |
| 4,865,022 | A | * | 9/1989 | Gorsen | 602/33 |
| 4,881,728 | A | | 11/1989 | Hunter | |
| 4,971,043 | A | | 11/1990 | Jones | |
| 4,995,378 | A | | 2/1991 | Dyer et al. | |
| 5,129,881 | A | | 7/1992 | Pope | |
| 5,146,641 | A | | 9/1992 | Zwickey | |
| 5,147,287 | A | | 9/1992 | Jewell et al. | |
| 5,177,823 | A | | 1/1993 | Riach | |
| 5,181,904 | A | * | 1/1993 | Cook et al. | 602/32 |
| 5,312,323 | A | * | 5/1994 | McAninch | 602/32 |
| 5,401,236 | A | | 3/1995 | Summerville | |
| 5,403,269 | A | * | 4/1995 | Kennedy | 602/36 |
| 5,512,040 | A | * | 4/1996 | Mathews | 602/36 |
| 5,577,802 | A | * | 11/1996 | Cowan et al. | 297/301.2 |
| 5,658,245 | A | * | 8/1997 | McGinnis et al. | 602/32 |
| 5,672,157 | A | * | 9/1997 | Gallagher et al. | 602/32 |
| 5,676,158 | A | * | 10/1997 | Katzman et al. | 128/845 |
| 5,681,272 | A | * | 10/1997 | Lee | 602/32 |
| 5,788,659 | A | * | 8/1998 | Haas | 602/36 |
| 5,957,876 | A | * | 9/1999 | D'Amico | 602/33 |
| 5,967,999 | A | * | 10/1999 | Hulicsko et al. | 602/32 |
| 5,997,494 | A | * | 12/1999 | Watkins et al. | 602/36 |
| 6,045,525 | A | * | 4/2000 | Chitwood | 602/36 |
| 6,113,563 | A | * | 9/2000 | D'Amico et al. | 602/32 |
| 6,113,564 | A | * | 9/2000 | McGuire | 602/32 |
| 6,238,361 | B1 | * | 5/2001 | Poirier | 602/33 |
| 6,258,050 | B1 | * | 7/2001 | Henderson | 602/33 |
| 6,506,174 | B1 | * | 1/2003 | Saunders et al. | 602/33 |
| 6,511,450 | B1 | * | 1/2003 | Bauermeister | 602/33 |
| 6,533,743 | B1 | * | 3/2003 | Moss | 602/32 |
| 6,547,809 | B1 | * | 4/2003 | Cuccia | 606/242 |
| 6,733,470 | B1 | * | 5/2004 | DeGeorge et al. | 602/32 |
| 6,899,690 | B2 | * | 5/2005 | Saunders et al. | 602/36 |
| 6,971,997 | B1 | * | 12/2005 | Ryan et al. | 602/32 |
| 6,994,683 | B1 | * | 2/2006 | Starr | 602/32 |
| 7,033,333 | B1 | * | 4/2006 | Croft et al. | 602/36 |
| 7,052,479 | B2 | * | 5/2006 | Drennan | 602/32 |
| 2003/0088200 | A1 | * | 5/2003 | Saunders et al. | 602/32 |
| 2004/0029687 | A1 | * | 2/2004 | Hogg | 482/142 |
| 2006/0058720 | A1 | * | 3/2006 | Becerra et al. | 602/32 |

* cited by examiner

TRACTION DEVICE FOR PHYSICAL THERAPY

This application claims the benefit of U.S. Provisional Patent Application Ser. No. 60/409,519 filed Sep. 10, 2002.

BACKGROUND OF THE INVENTION

1. Field of the Invention

The present invention is related to physical therapy devices. More particularly, the present invention is related to devices for administering traction to regions such as the neck and or lumbar region of a patient. Even more particularly, the present invention is related to traction devices for home or office use which provide the option of administering traction in either a cyclical or non-cyclical manner. The present invention also pertains to force transferring devices which can be used in various therapeutic and/or exercise applications.

2. Description of Relevant Art

The need for suitable reliable force transferring devices suitable for use in a variety of therapeutic and/or exercise situations has been contemplated. Such devices can be efficaciously utilized in various traction devices adapted to deliver therapeutic traction force to anatomical regions such as spinal regions including the cervical spinal region, the lumbar spinal region, and the like.

The need for simple, low cost cervical traction devices which can be used at home to administer cervical traction to provide relief to patients with various musculo-skeletal disorders of the neck and back is well recognized. Heretofore there have been developed a great number of head halters or other devices which apply cervical traction through the head of the patient. Many of these devices engage the jaw of the patient while surrounding the head. These type of halters not only inhibit the ability of the patient to talk, they also cause aggravation of the temporomandibular (TMJ) points. As a device for administering cervical traction, these devices are less than desirable. Jaw-type head halters of this type pull from an axis offset from the spine and thereby apply an undesirable twisting moment (cervical extension) to the patient's head and neck contrary to most types of desired cervical traction. In most types of cervical traction situations, it is desirable to engage the head of the patient at the occipital area of the head rather than the chin so that the pulling axis is in straight alignment with the spine and so that the pulling force is concentrated along the posterior of the head where it is most beneficial.

Other types of devices for engaging the head to correct neck problems are cervical braces. Such braces, which are referred to as "halo type", actually contact the patient's head with pointed screws which are forced inward through the skin to make contact with the bone of the skull. Aside from the obvious pain which a patient must endure when this type of brace is employed, the potential for infection to the person's head at the points where the skin is broken is ever present.

In order to obtain effective cervical traction, heretofore, it has been necessary to go to a physical therapy department or office. At such locations cervical traction was applied using complex devices such as that described in U.S. Pat. No. 4,508,109 to Saunders which was reissued as RE 32,791. Such devices could be used to apply cervical traction. However, they were of limited value because their complexity meant that traction therapy was available to the patient only at limited locations where such devices could be permanently installed. As a result, the patient was able to obtain cervical traction less often than would have been desirable not only because of the inconvenience of having to go to such locations at only the appointed times but also because of the expense.

Therefore, it is highly desirable to provide a cervical traction device applying tractive force in a manner heretofore only available in a physical therapist's office which can be used by the patient at home at various intervals throughout the day so that the patient, with or without assistance, can receive the equivalent therapeutic benefits associated with more frequent cervical traction use. Unfortunately, many cervical traction devices for home use which have been developed previously are either extremely cumbersome, rely on jaw-type head halters, or fail to provide sufficient cervical traction force in a safe manner to be truly beneficial to the patient. Examples of such devices include U.S. Pat. No. 4,971,043 to Jones; U.S. Pat. No. 5,129,881 to Pope; U.S. Pat. No. 3,105,489 to Zivi; U.S. Pat. No. 4,674,485 to Swanson; and U.S. Pat. No. 2,954,026 to Spinks. Furthermore, none of the cervical traction devices for home use offer an effective tension cycling option.

Heretofore, most traction systems previously developed, employ actual weight members and pulley systems to exert the desired tractive force to apply cervical traction. Because these systems employ drop weights, various protection systems have been suggested to protect against or minimize shock force as the weight is raised or lowered. One such system is disclosed in U.S. Pat. No. 5,957,876 to D'Amico. Such systems tend to be complicated and generally require external mounting to a wall or door unit. Mounting such weight bearing systems directly to the treatment table is difficult as the effectiveness of the traction device is reduced when weights bearing members are positioned too closely to the treatment table.

Thus, it would be beneficial to provide a cervical traction device which would deliver traction force in the case of cervical traction. Such force is delivered through the skull proximate to the occiput region. Other therapeutic traction force may be delivered to suitable regions as desired or required. It is also desirable that the device provide traction force in a manner which is safe and beneficial to the patient-user. It is also desirable to provide a traction device and method for using the same which permits control over the course of physical therapy and its administration in concert with a program recommended by a patient's physician and physical therapist.

Finally, it is desirable that the traction device be one which can include a wall or table-mounted weightless tractive force device which can be readily and easily employed in a variety of situations.

SUMMARY OF THE INVENTION

Disclosed herein is a device and method for providing traction on a patient to address or alleviate various musculo-skeletal disorders such as occur in regions like the cervical spine or lumbar region. The device is configured to permit administration of traction in various settings. The device can be advantageously utilized by physical therapists and the like in suitable therapeutic settings. The traction device is designed to be used while the patient is lying on his or her back on a substantially horizontal surface such as a bed or other elevated support. The traction device can include a body contacting assembly adapted to releasably contact the patient's neck proximate to the occipital region when cervical traction is indicated or other appropriate regions as in the lower back where traction such as lumbar traction is indicated. The device also includes means for delivering tension force on the assembly, and a tractive force transferring system that includes a tension line connected to the assembly and to the tension exerting means. the patient, such that the patient-user can interrupt the tension force transferred to the tension line. The body contacting assembly can be a unit such as a head rest assembly, a lumbar assembly, or the like.

In the first embodiment, the aforementioned elements are configured to provide cyclic traction which alternates between of a traction load and complete rest. In the second embodiment of the present embodiment, the aforementioned elements are configured to provide cyclic and/or intermittent traction between a first traction force and a second traction force and include means for accomplishing this function.

The device includes a tractive force delivery mechanism which utilizes a gas spring having an adjustable load bearing pivot mechanism is mounted on a suitable treatment table or other mounting device to provide weightless tractive force.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

The present disclosure is directed to a weightless force transferring device suitable for use in various situations such as muscle exertion and/or therapeutic traction. The weightless force transfer device is disclosed as used in various traction applications. Various other uses in areas such as repetitive muscle exercise can be developed as desired or required.

Disclosed herein is a traction device in various embodiments that can be employed to provide traction to a desired anatomical region, for instance the cervical or lumbar regions of the spine.

The traction device disclosed herein provides a device and method whereby controlled cervical traction force can be administered effectively in a variety of locations such as the home or physical therapist's office in an economical manner. The device can be used in a therapeutic program to apply traction force in either an intermittent manner, cyclical manner or in a completely non-cyclical manner. In the cyclical mode of operation, cervical traction force is exerted, then released, over a prescribed period of time or a number of repetitions and alternates either between a first tractive force and a second lower tractive force or between a tractive force and a no-load phase. In the non-cyclical mode of operation, traction force is applied in an essentially constant manner for a prescribed period of time. When tractive force is applied in the intermittent manner, as that term is applied in this application, the amount of tractive force cycles between a total tractive load or "on" position and a partial tractive load position. The ability to adjust the tractive force exerted is available in any combination of intermittent, cyclical and non-cyclical operating modes.

The ability to cycle (i.e. release or reduce tractive tension) permits the overall amount of traction force exerted on the anatomical region to be increased. This is particularly advantageous as therapy progresses, where it may become necessary to employ elevated levels of tractive force to maximize therapeutic benefit. However, if tractive force is to be increased, the tractive force must be cycled rather than applied as static load to prevent injury which could occur if high levels of tractive force are exerted for prolonged periods of time. Cycling permits a greater tractive force to be applied with minimal risk of injury.

The traction device of the present invention is designed to be used with a patient in the supine position. The supine position permits relaxation of the neck muscles in order to permit optimal traction effectiveness.

Figure 2:
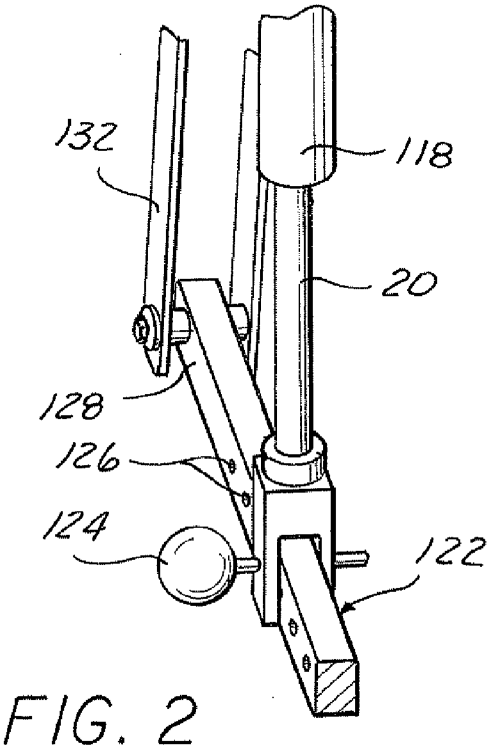
FIG. 2 is a detail of the adjustment mechanism depicted in FIG. 1.
Figure 1:
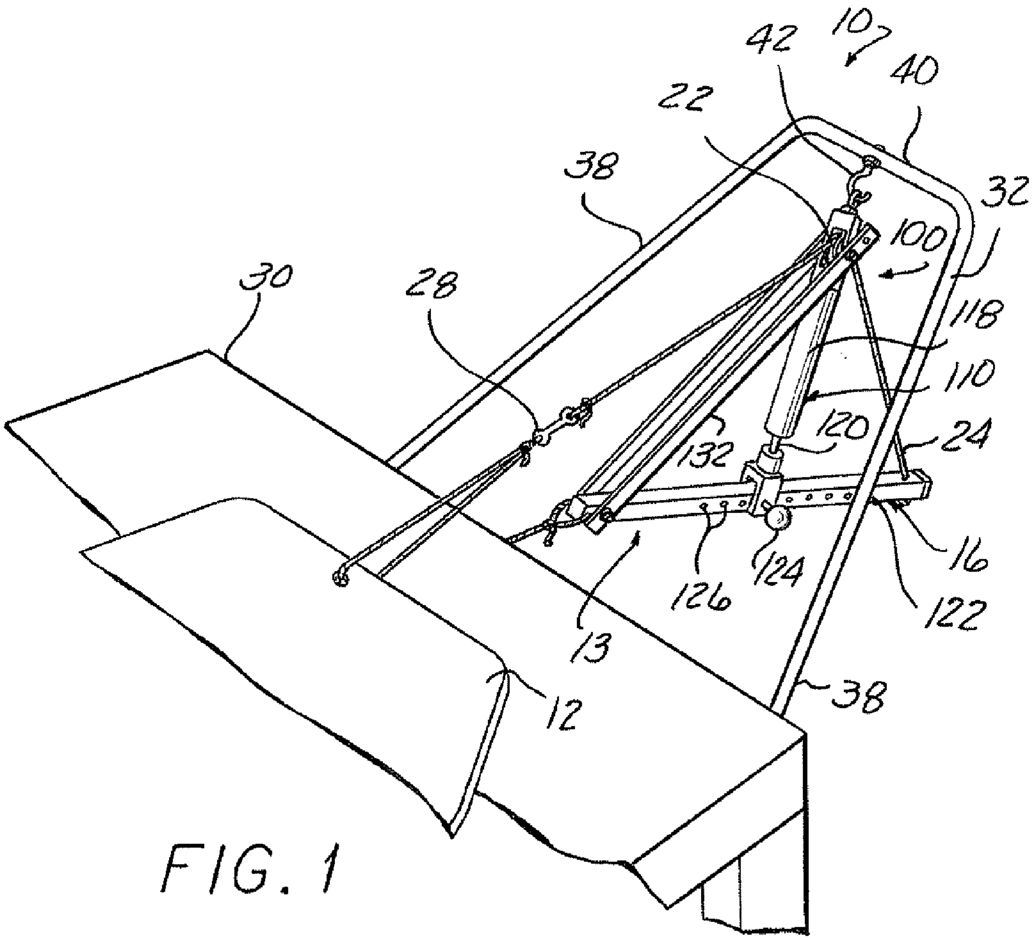
FIG. 1 is a perspective view of the weightless traction mechanism mounted to a treatment table.
Figure 3:
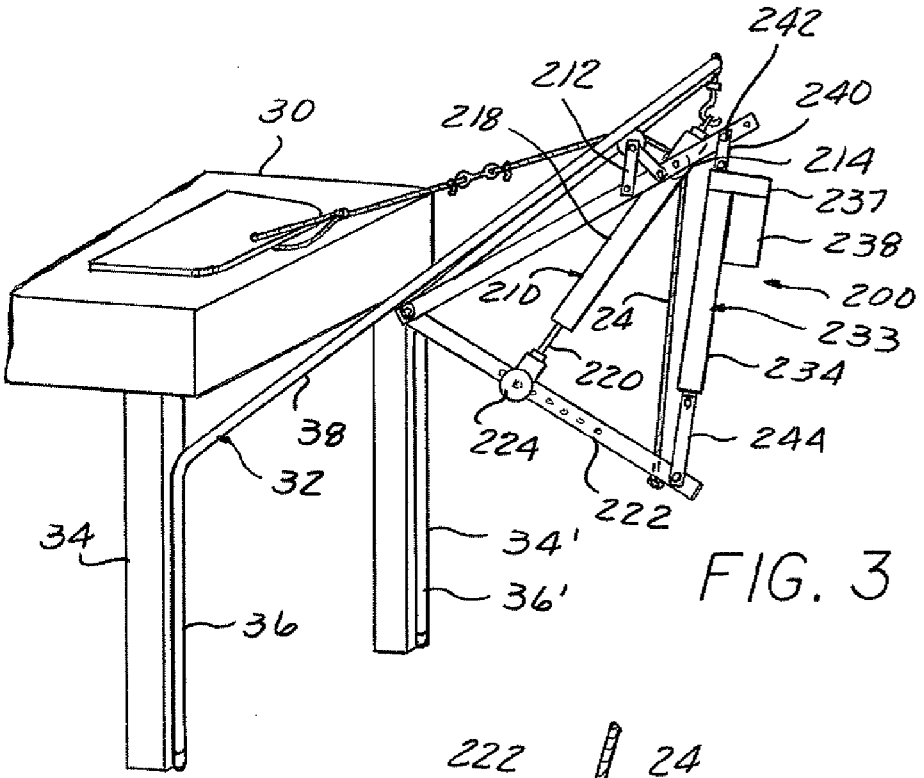
FIG. 3 is an alternate embodiment of the weightless force transfer mechanism having a motorized linear actuator utilized in a traction device.

In general as shown in FIGS. 1, 2, and 3, the traction device is composed of a body contacting assembly 12 to which a suitable tension transfer system 13 including tension line 24 is suitably attached. The tension transfer system 13 is capable of transferring a tractive force from the exerting tractive force delivery device 16 to the assembly 12. When the cyclical or intermittent mode of operation is required, the tractive force transfer system 13 of the traction device 10 also includes means for interrupting or varying the tractive force exerted on assembly 12. This tractive force interruption means includes a tension release line attached to the tension line 24 and terminating in a means for engaging an appendage of a patient such as a loop or suitable handle device. Such systems are discussed in U.S. Pat. Nos. 5,957,876 and 6,113,563 to Anthony T. D'Amico, which is incorporated herein by reference.

Figure 6:
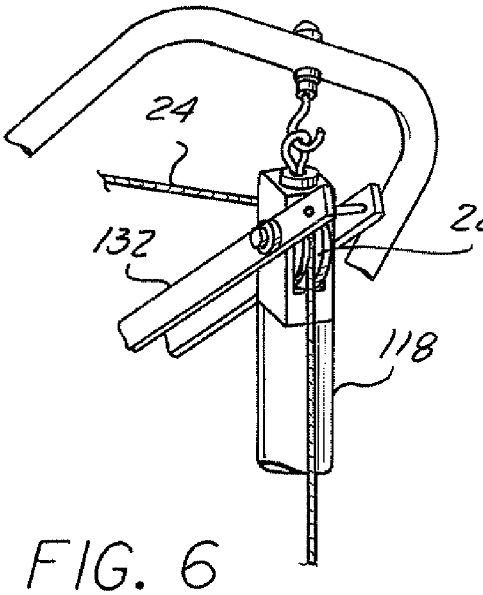
FIG. 6 is a detail view of the pulley mechanism and attachment means of an embodiment of the weightless traction mechanism.

The tractive force transferring system 13 can also include a suitable pulley mechanism such as pulley device 22. In the device of the present invention as shown in FIGS. 1 and 6, the tension line 24 extends through pulley device 22 and is moveable relative thereto. The pulley device 22 is adapted to be positioned at a suitable location relative to the body contacting assembly 12. Where desired or required, the pulley 22 may be elevated relative to the body contacting assembly to provide proper orientation for the body contacting assembly and administration of suitable tractive force.

The tension line 24 passes through the pulley device 22 in a manner such that the tension line 24 is provided with a first leg extending between pulley device 22 and body contacting assembly 12. The tension line 24 also includes a second leg 26 extending between pulley device 22 and the operative portion of the force transfer device.

Figure 5:
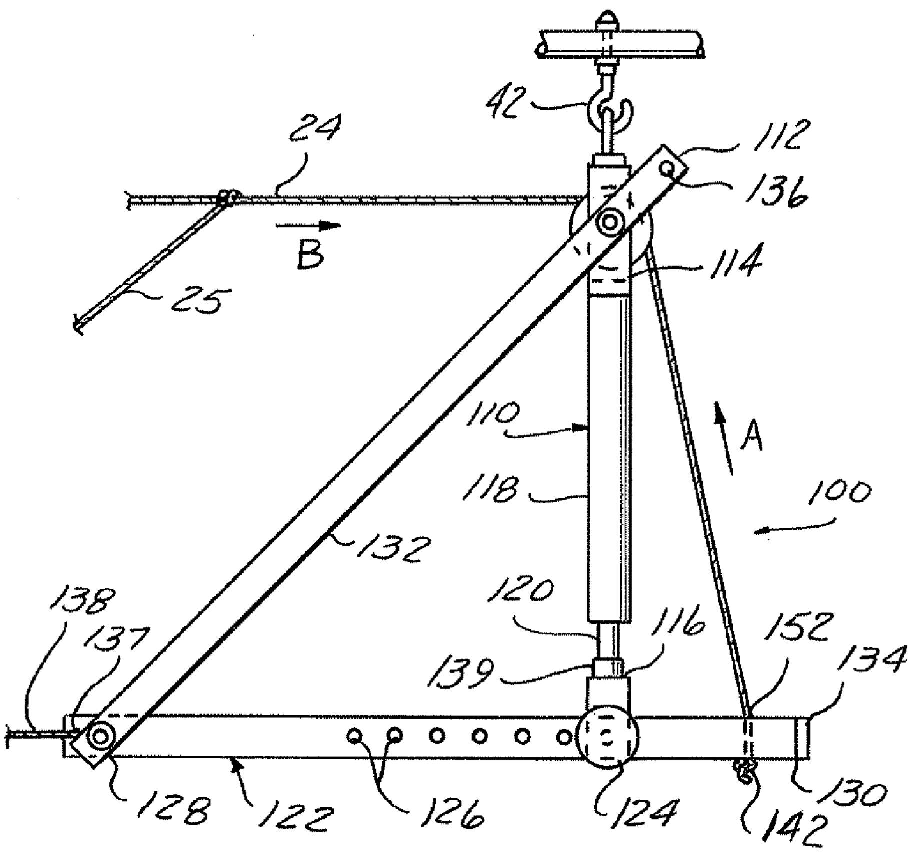
FIG. 5 is a schematic view of an embodiment of the weightless traction mechanism.

In the cyclical version cycle between traction load on and traction load off may be accomplished by suitable electronically or mechanically facilitated cycling devices. Alternately, a tension release line 25 (as shown in FIG. 5) may be attached to the tension line 24 at any suitable location as between the body contacting assembly 12 and the pulley 22. The tension release line may be configured in any suitable manner and may include means for attaching the tension release line to an appendage such as an arm or leg. Examples of such systems are discussed in the D'Amico patents previously referenced.

The tension line 24 may be equipped with a suitable means for adjusting the length of the first leg. Such means can include any type of adjustment device. The suitable adjustment devices can include rope sliders or other suitable mechanisms which would permit the proper adjustment of the tension line 24. The adjustment device can be located in either leg of the tension line 24. It is also possible to have adjustment devices located in both legs. As shown in FIGS. 1 and 3, the means for adjusting the length of the first leg 24 is a mechanical attachment and adjustment system 28.

The pulley device 22 may include a single pulley or a plurality of pulleys suitable for transferring tension to the body contacting assembly 12. As depicted in FIG. 1, a single pulley is employed to ensure that traction force is transferred to the assembly 12. In FIG. 3, multiple pulleys are employed.

The pulley device 22 is mounted at a height equal to or greater than the height of the body contacting assembly 12 above the floor F. As depicted in FIG. 1, the pulley device 22 is mounted such that the angle between the first and the second legs is less than 90°. It has been found that at such an angle, traction force, particularly cervical traction force, is most expeditiously transferred to the body contacting assembly 12 to be imparted to the patient in the manner to be described subsequently.

In the first embodiment of the traction device as disclosed, traction force may be imparted by a suitable mechanism far transferring traction force such as a tractive force delivery device 16. The tractive force delivery device 16 may engage the tension line 24 at any suitable location such as its terminal end 26.

The body contacting assembly 12 may have any suitable configuration that will facilitate engagement within a suitable region of the skull in the case of cervical traction or appropriate regions of the lower back where lumbar traction is employed. Examples of head rest assemblies suitable for use in administration of cervical traction are discussed in the D'Amico patents.

In using the cervical traction device 10 as depicted in FIGS. 1, 2, and 3, the tractive force delivery mechanism 16 is mounted to a suitable vertical support associated with treatment table 30. Mounting to the treatment table 30 can be by any suitable mechanism. As depicted in FIGS. 1, 2, and 3, a bracket 32 is affixed to table legs 34, 34' in any suitable essentially stationery manner. Bracket 32 includes lower mounting legs 36, 36' which are attached to table legs 34, 34'. An ascending arm 38, 38' is contiguously joined to each lower mounting leg 36, 36'. Ascending arms 38, 38' are joined to one another by mounting bar 40. Mounting bar 40 is essentially parallel to the head of the table to which it is mounted.

The tractive force delivery device 16 is mounted to the mounting bar 40 in any suitable permanent or removable manner. As shown in FIGS. 1, 2, and 3, the tractive force transfer device is mounted by hook 42 in a manner which permits appropriate movement of the tractive force delivery device relative to treatment bed 30.

In setting up and using the device 10, the tension line 24 is inserted through the pulley device 22 and adjusted for suitable length using the length adjustment mechanism such as linear linked device 28. The body contacting assembly 12 can be adjusted to accommodate the appropriate anatomical region of the patient-user and the tractive force delivery mechanism 16 can be adjusted to provide an amount of force sufficient to be tolerated by the patient-user and to effectively provide tractive therapy objectives which can include, but are not limited to, extension of the vertebrae in the effected region of the back. It is to be understood that the amount of tractive force will vary from patient to patient depending on the nature of the injury and the general physical condition of the individual patient-user. It is also to be understood that the amount of tractive force can vary during the course of treatment for a given individual due to changes in overall physical condition and in the healing experienced. The specific amount of force is that would be recommended by the physical therapist, physician or other health care professional.

When the traction device 10 of the present invention is in position, the patient is positioned in the unit and traction therapy commences. At the outset of each treatment session, it is desirable that there be no tractive force transferred through the tractive force transferring system 13 to the head rest assembly 12 to permit proper positioning of the patient-user. The opportunity to obtain the proper position in the unit. This can be accomplished in various ways—the patient-user can maintain force on the tension release line 18 (where applicable) with a foot or other appendage, or the weightless force transfer mechanism can be placed in a neutral, tension-free orientation.

The method for administering physical therapy using the device of the present invention in the cycling mode will now be described. Once the patient-user is in position in the device 10, the tractive force is applied to the appropriate anatomical region for an interval sufficient to provide therapeutic tractive force to the affected region. While this interval is patient-specific, it is generally understood that this interval will be an interval sufficient to provide extension without injury to surrounding tissue, i.e., less than 30 minutes. At the end of this interval, tractive force is released for a suitable rest interval. The rest interval is generally a period sufficient to provide relaxation of the affected region. Without being bound to any theory, it is believed that an interval of less than one minute with an interval of about 10 seconds being preferred will be effective in many instances. At the end of the rest interval, the tractive force is reinitiated.

A tractive force delivery device 100 suitable for use in traction devices that functions without weight bearing mechanisms is depicted in FIG. 5. The force delivery device 100 can be mounted on treatment table 30 by any suitable means. Alternately, it can be mounted, either temporarily or permanently, on a vertical surface, such as a wall or door, in a manner suitable to permit delivery and administration of tractive force.

The force delivery device 100 includes a suitably rated gas spring 110 having a first end 114 connected to a pulley mechanism 112. The gas spring member 110 also includes a lower end 116 distal to the upper end 114. The gas spring member 110 has a suitable outer housing 118 and an inner rod 120 telescopically received within the outer housing.

The gas spring 110 is mounted to the pulley mechanism 112 such that the outer housing 118 is proximate thereto. The gas spring 110 is configured such that the telescoping rod 120 is in an extended position relative to the outer chamber 118 when the device 110 is at rest.

The gas spring 110 of the force delivery device 100 has suitable means for attaching the distal end of the telescoping rod 120 to an appropriate adjustment member 122. The attachment member 124 may be any suitable pin, clamp, or other locking mechanism, such as a rod with suitable detent, which will permit secure but movable engagement between the attachment means 124 and the elongate member 122 suitable for adjusting the orientation of gas spring 110.

The elongate member 122 is typically an elongated member having a series of predetermined adjustment points located therein. As depicted in FIG. 5 the adjustment points are a series of through bores 126 through which the suitable rod or pin with detent can be attached. It is also within the purview of this invention that other suitable staged adjustment mechanisms be employed, such as appropriate placement grooves, clamping devices, or the like (not shown).

The elongate or adjustment member 122 has opposed first and second ends 128, 130 with suitable adjustment points 126 in spaced relation there between. As depicted at FIG. 11, the first end 128 of adjustment member 122 is movably attached to an ascending truss 132 which extends from a first point of elongate or adjustment elongate member 122 to a second point connected to with the pulley mechanism 112. The truss and elongate member 122 are connected so as to permit a scissors-like flexing between the two respective members depending upon the length of travel and pivot position of the telescoping rod 120 of the gas spring 110.

The second end 130 of the elongate member 122 is positioned distal to the first end 128. The second end 130 may include a suitable bumper cushion member 134 at the terminal end. Also included proximate to the second end 130 is a suitable means for attaching the terminal end of line 24. Line 24 may be secured to the elongate member 122 proximate to the second end 130 by a knot 26 by any other suitable essentially permanent means. As depicted in FIG. 5, attachment is through a suitable through bore 152 with an appropriate knot which can be modified to achieve adjustment in the ultimate length of line 24.

As can be seen from the drawing figures, the elongate member 122, gas spring 110, and ascending truss 132 form a triangular assembly which functions to achieve forward and rearward movement of line 24 relative to the length of the travel of gas spring 110. FIG. 5 depicts the mechanism in its compressed state with rod 120 retracted into the outer housing 118. This is accomplished by force exerted on line 24 in the direction of arrow A. Such compression as when force is exerted 24 by the user's appendage such as a foot and mechanism is released when the force on line 24 is decreased or discontinued. At that time, the gas spring begins to return to its precompressed state exerting reversed force in the direction of arrow B. This reverse force is translated into tractive force exerted on the body contacting assembly.

In the embodiment as depicted, a 35-pound rated gas spring is employed. It is to be understood that any rating could be successfully employed in the present invention depending upon the amount of tractive force required. As the gas spring is adjusted closer to the ascending truss 132, the angle between truss and gas spring is reduced. Closer movement toward the pivot point defined by 128, 132 results in less force being exerted ultimately on the line 24. Similarly, movement away from the ascending truss 132 results in greater tractive force being exerted.

The degree of force exerted can be quickly and accurately changed or modified quickly and efficiently as required by an individual user or between different users over time.

The device 100 of this embodiment also includes a suitable rotation stopper (i.e. pin), located in 136, which limits forward travel of the device around pulley mechanism 112. In this way, efficient maximized cyclical traction can be accomplished, as depicted in FIGS. 5 and 6. Other mechanisms that limit rotational travel of the device can be employed as desired or required.

The device 100 of the present invention may also include a stroke limiter. The stroke limiter may be a spacer such as spacer 139 located on rod 120 that limits the scissor action between members 122 and 132. The stroke limiter 139 serves to eliminate potential interference between element 116 and adjustment rod 122.

Figure 7:
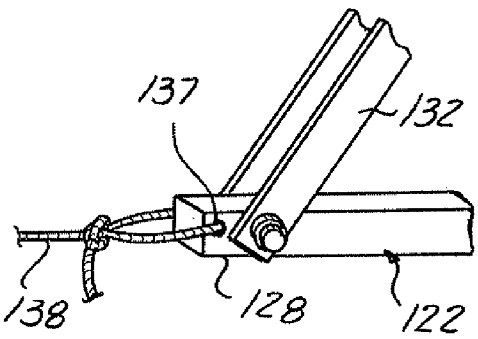
FIG. 7 is a detail of a rotational stop device employed in an embodiment of the weightless traction mechanism of FIG. 5.

The device 100 of the present invention also includes a suitable movement damper, for the table mount, which is connected to hole 137 located in adjustment member 122. The movement damper attached to 137 can be any means used to prevent vertical rotation of end 128 and is attached to the table or the table mount fixture used to mount the unit to the table. As depicted in FIG. 7, movement damper is rope 138.

In situations where the user operated cyclical traction unit as disclosed is employed, the cycled application and release of tractive force during a therapy session can be controlled by the patient. In such situations, the application and release of tractive force can be uniquely attuned to the physical indications experienced during each treatment session. Such patient control can provide subtle advantageous modifications of the general therapy regimen with each cycle in response to the physical conditions experienced. Additionally, control of the tractive force cycle by the patient can provide significant psychological benefits due to the restoration of control to the patient of an area of his health and well being after a period of disability. Finally, the user-operated traction device makes it possible for the patient-user to perform cyclic therapy using maximum tractive force multiple times during the course of a day or week in the comfort and privacy of his own surroundings.

Figure 4:
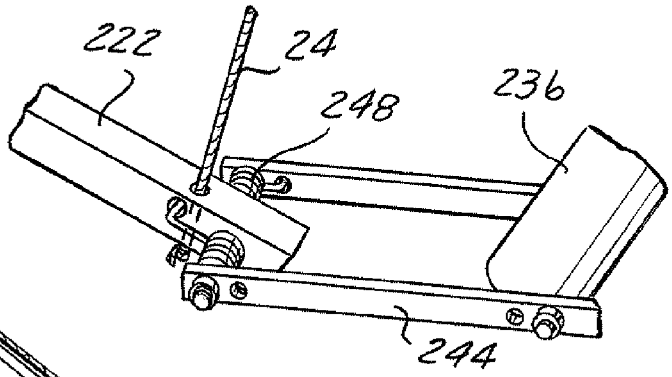
FIG. 4 is a detail view of the spring mechanism of FIG. 3 with the mechanism in full tractive force transferring mode.

An alternate tractive force delivery device 200, which functions with a motorized mechanism, is depicted in FIGS. 3, 4, and 8. The tractive force delivery device can be mounted on treatment table 30 by any suitable means. It is also contemplated that the tractive force delivery device 200 can be mounted, either temporarily or permanently, on a suitable surface as desired or required. Examples of these include the support table itself.

The force delivery device 200 includes a suitably rated gas spring 210 having an upper end 214 connected to a pulley mechanism 212. The gas spring member 210 has a suitable housing 218 and an inner rod 220 telescopically received within the outer housing.

The gas spring 210 is mounted to the pulley mechanism 212 such that the outer housing 218 is proximate thereto. Spring 210 is configured such that the telescoping rod 220 is in an extended position relative to the outer chamber 218 when the device 210 is at rest.

The gas spring member 210 of the force delivery device 200 has suitable means for attaching the distal end of the telescoping rod 220 to an appropriate adjustment member such as elongate member 222. The attachment means may be any suitable bolt, clamp, or other locking mechanism such as a pin with a suitable detent, which will permit secure but movable engagement between the attachment means 224 and the elongate member 222.

The elongate member 222 which can serve as adjustment member can be a rod or the like having a series of predetermined adjustment points located therein. As depicted in FIG. 3, the adjustment points are a series of through bores 226 through which the suitable bolt or pin with detent can be attached. Movement of the gas spring 218 from one adjustment point to another results in variation in the amount of tractive force delivered to the body contacting assembly.

It is also within the purview of this invention that other suitable staged adjustment mechanisms may be employed such as appropriate placement rubes or the like.

In the motorized embodiment of the tractive force delivery device, the elongate member 222 has opposed first and second ends 228, 230 with suitable adjustment mechanisms 222 in spaced relation therebetween. As best depicted in FIG. 8, the first end 228 of elongate member 222 is movably attached to an ascending truss 232, which extends from a first point in attachment with the elongated member 222 to a second terminal point region. The terminal point region is one that includes connection with the pulley mechanism 22 as well as connection with the linear actuator or other suitable compression mechanism. It is to be understood that the point of attachment for the pulley mechanism may also be the point of attachment for the gas spring 218 as desired or required.

The truss 232 and elongate member 222 are suitably attached to to one another permit a scissors-like flexing between the two respective members depending upon the length of travel and pivot position of the telescoping rod 220 of gas spring 210. The second end 230 of the elongate member 222 is positioned distal to the first end 228. The second end 230 may include a suitable bumper cushion member as desired or required at the terminal end 230. Also included proximate to the second end 230 is a suitable means for a motorized piston assembly device such as linear actuator device 233. Attachment can be by any suitable device permiting pivotal engagement between the two members.

As depicted, linear actuator 233 includes an outer body 234 and an inner rod 236 telescopically received within the outer body 234. The inner rod 236 can be telescopically movable relative to the outer body 234 by any suitable actuation means contained within the outer body 234 (not shown). The linear actuator may also include a suitable gear box 237 and a suitable drive mechanism 238 attached to the gear box 237. As depicted, the drive mechanism 238 is a suitable electromotor device that can be connected to suitable control circuitry and removably connected to a suitable power source (not shown). The control circuitry can include various switches for controlling the actuation and deactivation of linear actuator 233. Such switches and circuits can include, but are not limited to on-off switches as well as various sensor or monitoring devices, timers, and the like, as desired or required.

As can be seen from the relevant drawing figures, elongate member 222, gas spring 210, and ascending truss 232 form a triangular member that functions to achieve forward and rearward movement of line 24 relative to the length of travel of the gas spring 210. Linear actuator 233 functions to retract the gas spring telescoping rod 220 and load the gas spring as required to accomplish traction delivery.

In the alternate embodiment utilizing the linear actuator as depicted in FIGS. 8A, 8B, 8C, and 8D, the gear box 237 can be configured to include an upwardly projecting member 240 that is attached to the gear box 237 distal to the attachment of outer housing 234. The projecting member 240 can be fixedly or pivotally mounted to plate 240 as desired or required. As depicted plate 240 also includes attachment 242 for attaching the member 242 to truss 232. As depicted in FIGS. 8A, 8B, 8C and 8D, the attachment 242 is a pin adapted to secure mounting member 240 to truss 232 in a manner which permits pivotal movement. As depicted, the attachment means 242 is a suitable through pin extending through the parallel truss members 232 and engaging the mounting hole present in member 240.

Figure 9:
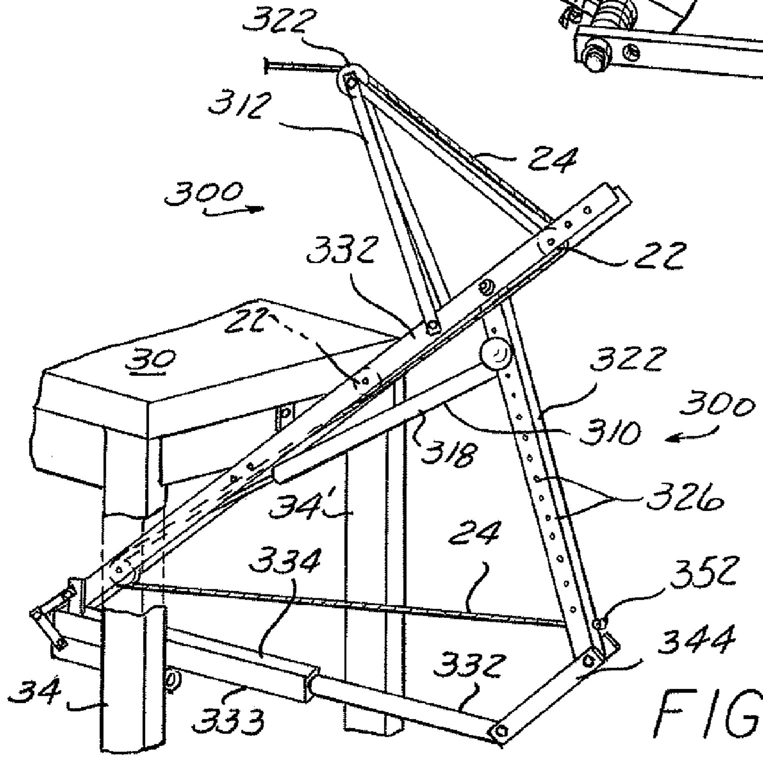
FIG. 9 is a weightless tractive force transferring mechanism for use with the lumbar region.

The second end 230 of adjustment rod 222 also includes suitable means for attaching the terminal end of line 24. Line 24 may be secured to the adjustment rod 222 proximate to the second end 230 by a suitable knot 250, or by any other suitable essentially permanent means. As used herein, the term "suitable essentially permanent" is taken to mean an attachment mechanism which will withstand multiple cycles of the traction device. As depicted in FIGS. 8 and 9, attachment is through a suitable through bore with an appropriate knot that can be modified to achieve adjustment of the ultimate length of line 24.

The linear actuator 233 also includes a rotatable arm member 244 pivotally attached to the distal end 242 of rod 236 and rotatably attached to elongate member 222 proximate to its second end 230. As depicted in the drawing figures, member 244 is configured as linkages that accomplish rotatable movement around a pivot point located at second end 230 of adjustment rod 222. Other configurations are contemplated which can facilitate the rotational movement discussed herein.

Figure 8A:
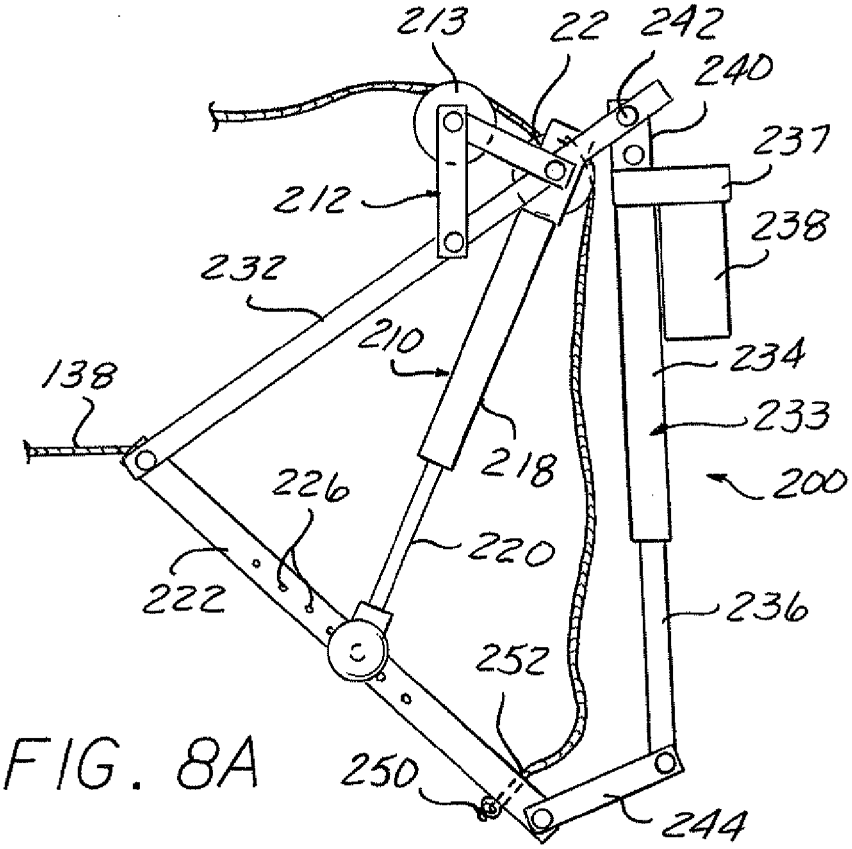
FIG. 8A is a perspective view of the tractive force transfer mechanism in the "off" position.
Figure 8B:
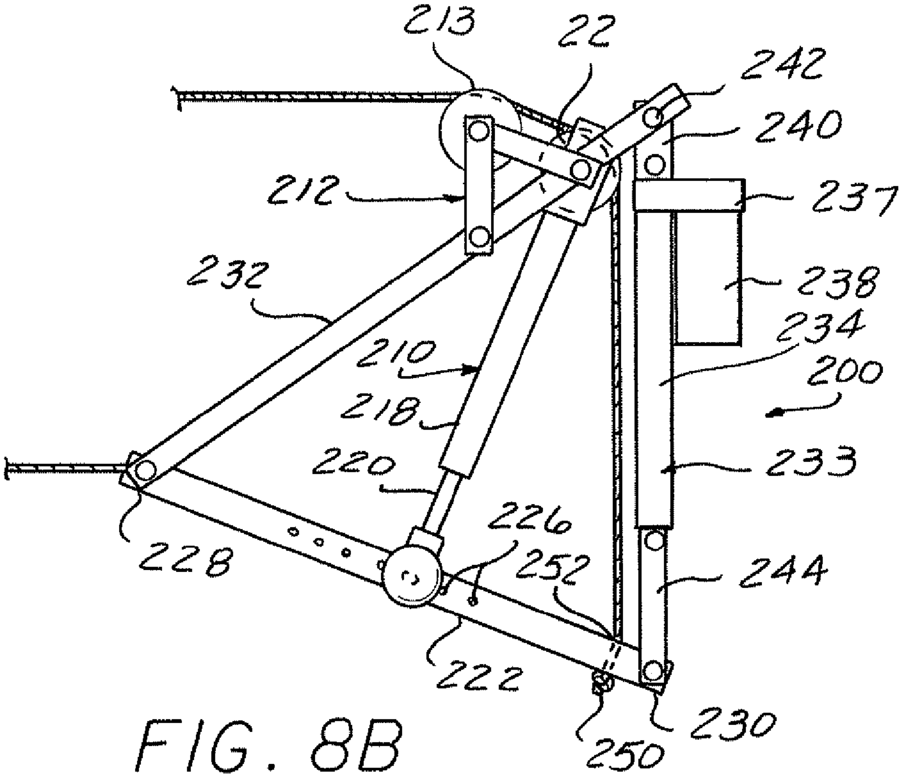
FIG. 8B is a perspective view of the tractive force mechanism in the start-up position.
Figure 8C:
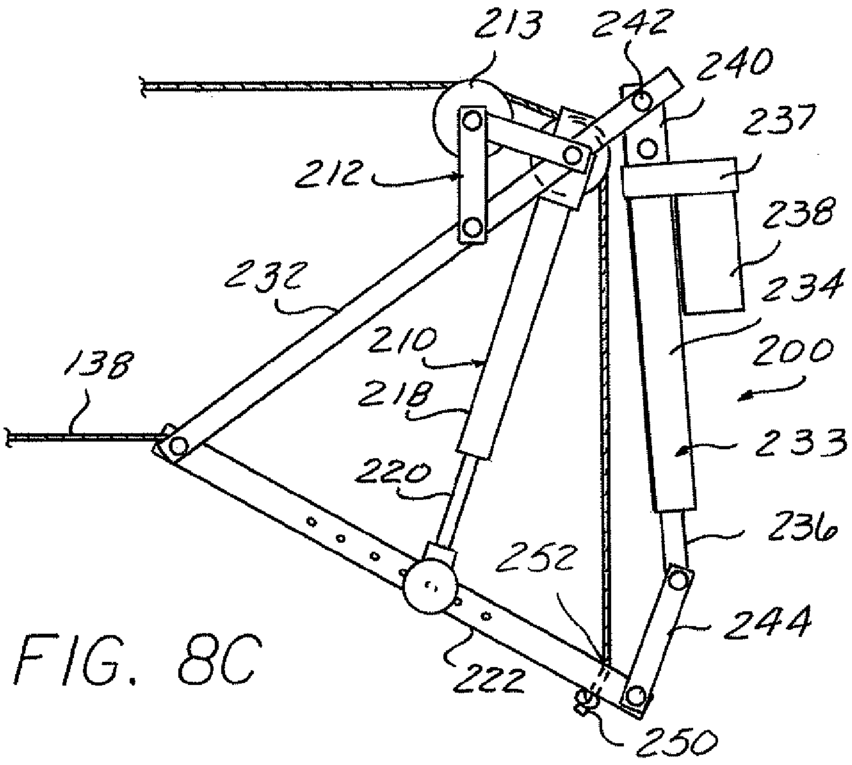
FIG. 8C is a perspective view of the tractive force transfer mechanism at the beginning of the load cycle.
Figure 8D:
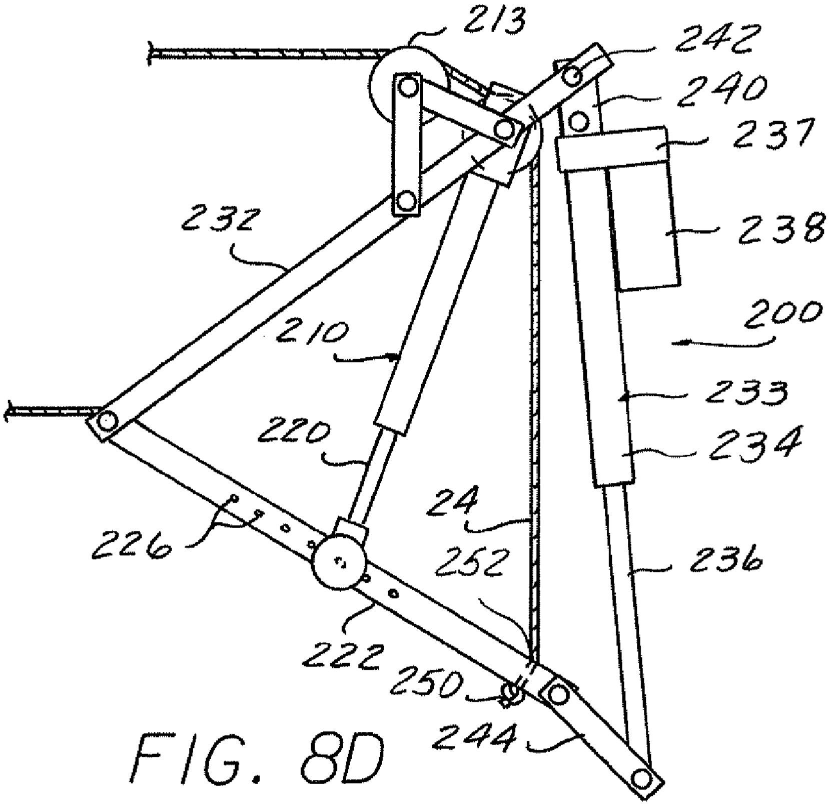
FIG. 8D is a perspective view of the tractive force transfer mechanism in the loaded position.

The cycle of movement of the tractive force delivery device 200 is outlined sequentially in FIGS. 8A, 8B, 8C, and 8D. In FIG. 8A, the device 200 is in the off position, gas spring 210 is extended and linear actuator 233 is in an extended position such that no force is exerted on tension line 24. In FIG. 8B, the device 200 is cycled to the patient set up position, in which the patient can be positioned in the body contacting assembly but experiences no tractive load. In the rest position, rod 236 is retracted into housing 234 and member 244 is drawn into a position essentially parallel to housing 234. FIG. 8C depicted the initiation of tractive force loading. Upon extension of the rod 236, member 244 pivots through a partially angled orientation and the gas spring begins to extend out. In FIG. 8D, the device 200 is in the fully loaded orientation. Gas spring 210 is extended and a tractive force is applied to the patient. Member 244 is rotated angularly to a position such as that depicted. Gas spring 210 now exerts force against the elongate member 222.

In order to provide for unimpeded rotation of the member 244 relative to the pivot point proximate to second end 230, the linear actuator 233 can include a suitable torsion spring member 248. As depicted in FIG. 4, torsion spring member 248 includes a pair of spring elements positioned between the respective arms of member 244 and the second end 230 of adjustment rod 220. Spring member 248 is configured to provide biasing movement of the member 244 relative 230.

The gas spring 110, 210 can be of any suitable rating. Typically gas springs rated between 10 and 250 pounds can be utilized depending on the configuration and tractive force required. In the embodiment as depicted, a 35-pound rated gas spring is employed. However, it is to be understood that any rating could be successfully employed in the present invention depending upon the amount of tractive force required. As the gas spring is adjusted closer to the ascending truss 232, the angle between truss and gas spring is reduced. Closer movement toward pivot point proximate to the ascending truss 132, 232 results in less force being exerted ultimately on line 24. Similarly, movement away from the ascending truss 132, 232 results in greater force.

The device such as device 200 can also include a suitable pulley adjustment assembly 214, which includes an adjustable mounting bracket 212 for adjusting the height of pulley 213 relative to a sending truss 232. In this manner, the angular position of the body contacting assembly relative to the tractive force transferring device can be accomplished.

As depicted in FIGS. 8 and 9, the device is mounted to a table by a suitable bracket 32. Preferably, the device can be removably mounted by a suitable hook or the like to facilitate free movement of the tractive force transferring device and to permit easy adjustment and the like.

The cycle of traction and rest can be repeated for a period prescribed by the patient's physician, physical therapist or other health care giver. The interval can be defined by elapsed time or cycle repetitions as desired and tolerated by the individual patient-user. In order to time the cycles, suitable timing mechanisms and/or programs can be utilized as desired or required. The cyclical repetition of alternating rest and traction intervals enables the user to employ and tolerate greater traction force than would be possible if non-cyclical cervical (static) traction were employed. The particulars regarding cyclic mode of operation typically would be chosen by the physician or therapist. The greater traction weight is desirable as it accomplishes greater extension of the affected region such as the neck or lumbar region with associated enhanced therapeutic benefits.

In various instances, cyclical or intermittent cervical traction may not be necessary or warranted. It is also contemplated that a non-cyclical applications of the weightless tractive force transferring device can be accomplished. When the non-cyclical device is employed, the patient-user is placed in position and tractive force is applied to the neck region for a continuous interval. As with the cyclical cervical traction device described previously, the amount of tractive force and the total cervical traction interval are patient specific and should be recommended by a physician, physical therapist, or other qualified health care professional on a case-by-case basis based on individual needs and requirements.

In either situation, use of either the cyclic, intermittent, or non-cyclic cervical traction device of the present invention permits the patient-user to engage in cervical traction at home, at a suitable physical therapy location or where convenient. Thus, it is contemplated that traction therapy can be performed more readily and frequently as desired.

The increased therapy frequency has the potential of reducing the total interval the patient would require therapy and providing benefits to the patient such as an alleviation of pain in a shorter period of time. Use of the traction unit disclosed herein in the home or clinic provides the additional advantage in that the patient can obtain a clinical equivalent of cervical traction when needed during the day at home rather than waiting until the next scheduled visit to the physical therapist. Prompt alleviation of pain and discomfort can prevent further patient debilitation and can actually promote healing in some instances. Additionally, the ability to employ traction in the home as needed can actually assist in the restoration of normal sleep patterns as cervical traction can be performed in bed immediately prior to sleep. The unit can be removed while the patient is in the supine position thereby preventing the affected region from experiencing a potentially painful compressive load prior to sleep.

It is also contemplated that the motorized weightless tractive force mechanism can be advantageously employed to provide cyclical, intermittent, or continuous tractive force to various anatomical regions. Depending on the nature of the tractive force to be applied, the device as disclosed herein can be oriented in any manner that will achieve an implement appropriate traction. An alternate embodiment of the device as disclosed herein is depicted which is suitable for delivery of traction to the lumbar region of the spine. As depicted in FIG. 9, the device 300 is mounted such that truss 332 is attached to table 30. The gas spring 310 is movably attached to elongate member 322 to form a triangle therebetween. A suitable motor actuated piston assembly such as linear actuator 333 can be suitably positioned or mounted relevant to table T and can include an outer housing 334 and an elongate member 336 telescopically positioned movable to housing 334. Linear actuator 333 can also include member 344 adapted to the pivotally rotatable relative to second end 330 of adjustment bar 322. The tension line 24 can be connected to the device a a suitable location on elongate member 322 and can be fed through suitable pulleys such as pulley device 312. Tension line 24 can be affixed relative to the elongate member 322 in any suitable manner such as by knot 352. The elongate member 322 can include suitable adjustment means such as bore holes 326. Gas spring 318 can be connected to the elongate member 322 in the manner depicted in FIG. 9.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A traction device for use on a support surface comprising:

a body contacting assembly adapted to releasably contact an anatomical region of a patient;

a tractive force exerting apparatus capable of exerting force on the body contacting assembly, the tractive force exerting apparatus configured to move independently relative to the support surface, the tractive force exerting apparatus including:

(a) a gas spring member variable between an extended rest position and a retracted force exerting position, the gas spring having an upper end and an opposed lower end;

(b) an elongate member adjustably attached to a lower end of the gas spring;

(c) a truss having a first end region and a second end region, the first end region located a spaced distance from the lower end of the gas spring and the second end region located proximate to the elongate member, wherein the truss is in pivotal connection with the elongate member, wherein the gas spring, the elongate member and truss cooperatively forming a triangular assembly;

a tractive force transferring system, the tractive force transferring system including a tension line having a first end and a second end, the first end connected to the body contacting assembly, the second end connected to the tractive force exerting apparatus.

2. The traction device of claim 1 further wherein the traction force exerting assembly comprises a pulley mechanism located proximate to an upper end of the gas spring, wherein the tension line extends through the pulley mechanism from a point of attachment with the body contacting assembly to a point of attachment with the elongate member of the tractive force exerting mechanism.

3. The traction device of claim 1 wherein the tractive force transferring means is mounted to the support surface.

4. The traction device of claim 1 wherein the support surface is a table, wherein the traction device further comprises at least one mounting bracket affixed to the table, the tractive force exertion apparatus mounted on the mounting bracket.

5. The traction device of claim 1 wherein the body contacting assembly is configured to engage a body proximate to at least one of the cervical region or lumbar region.

6. The traction device of claim 1 further comprising a tension release line, the tension release line having a first end connected to the tension line and a second end configured to releasably contact an appendage of a patient utilizing the device.

7. A traction device for use on a support surface comprising:

a body contacting assembly adapted to releaseably contact an anatomical region of a patient;

tractive force exertion apparatus capable of exerting tractive force on the body contacting assembly, the tractive force exertion apparatus including a gas spring member having an upper end and a lower end, the gas spring member variable between an extended rest position and a retracted force exerting position; and means for retracting the gas spring member into the force-retracting position, a tractive force transferring system connected between the body connecting assembly and the tractive force extension apparatus;

wherein the tractive force exerting apparatus further includes:

a pulley mechanism located proximate to the upper end of the gas spring;

an elongate member adjustable attached to the lower end of the gas spring; and a truss pivotally attached to the elongate member, the truss having a first end region and a second end region, the first end region pivotally connected to the elongate member and located a spaced distance from the lower end of the gas spring, the second end region connected proximate to the pulley mechanism and proximate to the upper end of the gas spring member;

wherein a tension line extends through the pulley mechanism from a point of attachment with the body contacting assembly to a point of attachment with the elongate member of the tractive force exertion apparatus.

8. The traction device of claim 7 wherein the gas spring retraction means comprises a tension release line, the tension release line connected to the tension line and terminating in a structure suitable for releasable contact with an anatomical region of a patient.

9. The traction device of claim 7 wherein the gas spring refraction means further comprises a stroke limiter, the stroke limiter associated with a rod telescopically extending from the gas spring.

10. The traction device of claim 7 further comprising a bumper member, the bumper member attached to elongate member at a location distal to the truss.

11. The traction device of claim 7 wherein the gas spring refraction means comprises a motorized mechanism.

12. The traction device of claim 11 wherein the motorized mechanism comprises;

a linear actuator having a telescopically projecting member;

at least one linkage having a first end and an opposed second end, the linkage pivotally attached to the telescopically projecting member at the first end and pivotally attached to the elongate member at the second end, and a motor actionable on the linear actuator.

13. The traction device of claim 12 further comprising at least one torsion spring, the torsion spring positioned at the pivotal connection between the linkage and the elongate member.

14. The traction device of claim 7 wherein the tractive force exertion apparatus further comprises:

a linear actuator positioned between and in contact with the elongated member and truss; and a power supply mechanism capable of cycling the linear actuator.

15. The traction device of claim 14 wherein the tractive force exertion apparatus further comprises at least one linkage rotationally mounted between the linear actuator and the elongate member, wherein the linkage is moveable between a first rest position and a at least a second actuated position, wherein the linkage permits the gas spring to exert force on the tension line upon extension of the linear actuator yet allows the linear actuator to compress the gas spring when it is retracted.

16. The traction device of claim 7 wherein the tractive force transferring system further comprises at least one pulley assembly, the pulley assembly including a pulley in moveable engagement with the tension line and means for mounting the pulley assembly on the tractive force exertion apparatus at a location proximate the gas spring.

17. The traction device of claim 16 wherein the pulley assembly further includes at least one additional pulley and an adjustable triangular mounting assembly, the additional pulley rotatably mounted on an adjustable triangular mounting assembly, the triangular mounting assembly connected to either the elongate rod or the truss such that the at least one additional pulley is positioned at a spaced distance from the member to which it is connected.

18. The traction device of claim 7 wherein the body contacting assembly is configured to engage a body proximate to at least one of the cervical region or lumbar region.

19. The traction device of claim 7 further comprising rotational stop member, the rotational stop member located on the truss positioned adjacent to a junction between the truss and the pulley assembly.

20. A traction device for use on a support surface comprising:

a body contacting assembly adapted to releasably contact an anatomical region of a patient;

a tractive force exerting apparatus capable of exerting force on the body contacting assembly, the tractive force exerting apparatus configured to move independently relative to the support surface, the tractive force exerting apparatus including:

(a) a gas spring member variable between an extended rest position and a retracted force exerting position, the gas spring having an upper end and an opposed lower end;

(b) an elongate member adjustably attached to a lower end of the gas spring;

(c) a truss having a first end region and a second end region, the first end region located a spaced distance from the lower end of the gas spring and the second end region located proximate to the elongate member, wherein the truss is in pivotal connection with the elongate member;

a tractive force transferring system, the tractive force transferring system including a tension line having a first end and a second end, the first end connected to the body contacting assembly, the second end connected to the tractive force exerting apparatus, wherein the traction force exerting assembly comprises a pulley mechanism located proximate to an upper end of the gas spring, wherein the tension line extends through the pulley mechanism from a point of attachment with the body contacting assembly to a point of attachment with the elongate member of the tractive force exerting mechanism, and wherein the pulley assembly further includes at least one additional pulley and an adjustable triangular mounting assembly, the additional pulley rotatably mounted on an adjustable triangular mounting assembly, the triangular mounting assembly connected to either the elongate rod or the truss such that the at least one additional pulley is positioned at a spaced distance from the member to which it is connected.

21. A traction device for use on a support surface comprising:

a body contacting assembly adapted to releasably contact an anatomical region of a patient;

a tractive force exerting apparatus capable of exerting force on the body contacting assembly, the tractive force exerting apparatus including:

(a) a gas spring member variable between an extended rest position and a retracted force exerting position, the gas spring having an upper end and an opposed lower end;

(b) an elongate member adjustably attached to a lower end of the gas spring;

(c) a truss having a first end region and a second end region, the first end region located a spaced distance from the lower end of the gas spring and the second end region located proximate to the elongate member, wherein the truss is in pivotal connection with the elongate member;

a tractive force transferring system, the tractive force transferring system including a tension line having a first end and a second end, the first end connected to the body contacting assembly, the second end connected to the tractive force exerting apparatus; and a tension release mechanism, the tension release mechanism actionable on the tension line to release tractive force, the tension release mechanism including a motorized assembly actionable on the tension line to release on the tension and a power supply for the motorized assembly;

wherein the tension release mechanism comprises:

a linear actuator positioned between and in contact with the elongated member and truss; and a linkage rotationally mounted between the linear actuator and the elongate member, wherein the linkage is moveable between a first rest position and a second retracted position, wherein the linkage permits the gas spring to exert force on the tension line upon extension of the linear actuator yet allows the linear actuator to compress the gas spring when it is retracted.

22. The traction device of claim 21 wherein the tractive force transferring means is mounted to the support surface and wherein the support surface is a table, wherein the traction device further comprises at least one mounting bracket affixed to the table, the tractive force exertion apparatus mounted on the mounting bracket.

23. The traction device of claim 21 further wherein the traction force exerting assembly comprises at least one pulley mechanism located proximate to an upper end of the gas spring, wherein the tension line extends through the pulley mechanism from a point of attachment with the body contacting assembly to a point of attachment with the elongate member of the tractive force exerting mechanism.

24. The traction device of claim 21 further comprising at least one torsion spring, the torsion spring positioned at the pivotal connection between the linkage and the elongate member.

25. The traction device of claim 21 wherein the pulley assembly further includes at least one additional pulley and an adjustable triangular mounting assembly, the additional pulley rotatably mounted on an adjustable triangular mounting assembly, the triangular mounting assembly connected to either the elongate rod or the truss such that the at least one additional pulley is positioned at a spaced distance from the member to which it is connected.

* * * * *